US006826313B2

(12) United States Patent
Robar et al.

(10) Patent No.: US 6,826,313 B2
(45) Date of Patent: Nov. 30, 2004

(54) METHOD AND AUTOMATED SYSTEM FOR CREATING VOLUMETRIC DATA SETS (75) Inventors: James L. Robar, Vancouver (CA); Brenda G. Clark, Vancouver (CA)

(73) Assignee: The University of British Columbia, Vancouver (CA)

(*) Notice: Subject to any disclaimer, the term of this patent is extended or adjusted under 35 U.S.C. 154(b) by 575 days.

(21) Appl. No.: 09/828,172

(22) Filed: Apr. 9, 2001

(65) Prior Publication Data

US 2001/0033682 A1 Oct. 25, 2001

Related U.S. Application Data (63) Continuation of application No. PCT/CA00/00920, filed on Aug. 9, 2000.
(60) Provisional application No. 60/147,485, filed on Aug. 9, 1999.

(51) Int. Cl.[7] .............................. G06K 9/36; H05G 1/42; A61B 5/05; G06T 17/00
(52) U.S. Cl. ........................ 382/287; 382/132; 378/97; 600/414; 345/424
(58) Field of Search ................................. 382/284–300, 382/312, 128–134, 154, 181, 216, 304; 378/1, 20, 21, 28, 97, 62, 163, 205; 600/407, 414; 345/424, 653

(56) References Cited

U.S. PATENT DOCUMENTS

| | | | | |
|---|---|---|---|---|
| 5,070,454 A | * | 12/1991 | Griffith | 378/163 |
| 5,113,357 A | * | 5/1992 | Johnson et al. | 345/424 |
| 5,250,019 A | | 10/1993 | McGinley | |
| 5,511,107 A | | 4/1996 | Sliski | |
| 5,633,584 A | | 5/1997 | Maryanskl et al. | |
| 5,635,709 A | | 6/1997 | Sliski et al. | |
| 5,671,265 A | * | 9/1997 | Andress | 378/98.11 |
| 5,891,030 A | * | 4/1999 | Johnson et al. | 600/407 |
| 6,154,518 A | * | 11/2000 | Gupta | 378/62 |

FOREIGN PATENT DOCUMENTS

EP 0853920 7/1998

\* cited by examiner

Primary Examiner—Kanji Patel
(74) Attorney, Agent, or Firm—Oyen Wiggs Green & Mutala

(57) ABSTRACT

A method for creating a volumetric data set representing a three-dimensional distribution, such as a dose distribution produced by a radiosurgery system uses a plurality of stacked sensors (12) to obtain two-dimensional cross sectional images of the distribution. The images are optically scanned in a scanner (20) to obtain digitized two-dimensional images which can be processed by software in a computer (22). Each of the sensors (12), which may be, for example, a sheet of X-ray sensitive film, is marked with a visible fiducial mark (17). The software locates images of the fiducial marks (17) in the digitized images. The locations of the fiducial marks (17) indicate the proper orientation and sequence of each image. The software populates a volumetric data structure with data from the scanned images. Interpolation may be used to increase the resolution of the data structure. The system is not susceptible to errors which might be caused by images of the sensors being inverted or mis-aligned before or during scanning.

20 Claims, 9 Drawing Sheets

FIG. 9C

METHOD AND AUTOMATED SYSTEM FOR CREATING VOLUMETRIC DATA SETS

CROSS REFERENCE TO RELATED APPLICATIONS

This application is a continuation of PCT international application No. PCT/CA00/00920 which designates the United States of America, which is entitled METHOD AND AUTOMATED SYSTEM FOR CREATING VOLUMETRIC DATA SETS, and is hereby incorporated herein by reference. This application claims the benefit of the filing date of U.S. application No. 60/147,485 filed on 9 Aug. 1999.

TECHNICAL FIELD

This invention relates to the creation of volumetric data sets from multiple two-dimensional analog images. Embodiments of the invention provide both methods for assembling a number of two-dimensional images into a volumetric data set and automated systems for performing such methods. The invention has particular application in the generation of volumetric data sets representing the spatial distribution of absorbed radiation dose for radiation exposures to be used in conformal radiosurgery.

BACKGROUND

There are various situations in which it is necessary to obtain a volumetric data set which represents the spatial distribution of some physical quantity. In many such cases there is no practical cost effective way to directly acquire data for the volumetric data set. Radiosurgery is one such situation.

Radiosurgery uses radiation beams to treat tumours. It is desirable to provide dose distributions which provide high doses within a tumour being treated and low doses everywhere else. Conventional linear accelerator-based stereotactic radiosurgery employs a number of circular photon beams or beam arcs to create sharply defined, but approximately spherical or ellipsoidal dose distributions.

The inherent symmetry of dose distributions produced by circular beams permits the actual dose distribution to be measured by taking 1 or 2-dimensional profiles using standard dosimetry techniques.

Many tumours, however are not spherical or ellipsoidal. It is desirable to provide shaped dose distributions to treat such tumours. Technology for the delivery of irregularly-shaped dose distributions has evolved rapidly. Radiosurgery systems which employ technologies such as fixed conformal collimation, dynamic conformal collimation, micro-multileaf collimation and intensity modulated radiation therapy are able to create non-spherical volumetric dose distributions suitable for treating non-spherical lesions. A dose distribution may be provided by way of a planned series of exposures to radiation. Various dose calculation algorithms may be used to mathematically model the dose which will be provided by a given configuration of a radiosurgery system. While the sophistication and accuracy of dose calculation algorithms has increased, it is necessary to be able to measure the actual volumetric dose distribution provided by a radiosurgery system apparatus so as to ensure that the apparatus is functioning properly and is producing the predicted dose distribution. Radiosurgery systems should provide the predicted dose distribution within a spatial accuracy of about ±1 mm or better and a numerical accuracy of about ±5%, preferably ±2%, or better throughout the volume of the dose distribution. Measuring such distributions requires a dosimeter capable of measuring integrated dose in three-dimensions.

Traditional dosimeters, such as miniature ion chambers, thermoluminescent dosimeters, diodes and diamond detectors have been used for radiosurgical dosimetry but measure doses only at single points or along one-dimensional lines (U.S. Pat. No. 5,635,709 describes an example of a system which senses radiation intensity at a point). Ferrous sulfate and BANG gel dosimetry techniques (for example, see U.S. Pat. No. 5,633,584 which describes a system for 3-dimensional dosimetry which uses a polymerizable gel) provide 3D maps of administered dose. However, both of these methods remain expensive because an NMR scanner is required for dose calibration and readout. The gels also require special handling. Further, the use of NMR to read out dose data imposes significant limitations on BANG or Fricke gel dosimetry in terms of achievable spatial resolution and signal-to-noise ratio.

Radiographic and radiochromic films are inherently planar dosimeters. Such films can be placed in the path of a photon beam to provide a two-dimensional dose profile. The dose profile may be obtained by scanning the film using a conventional densitometers or CCD-based digitizer. Radiographic and radiochromic films provide the advantages of sub-millimeter spatial resolution and high signal-to-noise ratio. Such films are affordable and accessible.

Radiographic films typically have silver halide emulsions which are exposed by interaction with photons. After exposure the films are developed. For larger (i.e. >10 cm×10 cm) conventional radio-therapy photon fields, however, the accuracy of radiographic film dosimetry has been limited by the over response of silver halide film emulsions to low energy scattered photons. Below energies of approximately 400 keV, the mass attenuation coefficient of typical emulsions diverges rapidly from that of tissue. Therefore, changes in the photon population in this low-energy region cause variations in emulsion sensitivity. This effect produces a systematic shift in the optical density-to-dose sensitometric calibration curve with depth thus necessitating corrections to the measured optical density distributions.

Fortunately, small (less than about 40 mm in diameter) high energy, for example 6 MeV, radiosurgical photon beams exhibit spectra composed predominantly of primary photons. The inventors have conducted Monte Carlo simulations which have demonstrated that, unlike large radiotherapy photon fields, in small radiosurgical beams increases in the spectral component below 400 keV are negligible to depths of 20 cm. Typically 5% or less of the incident spectrum in a 6 MeV radiosurgical photon beam exists in this low-energy region. The majority of the spectral population is found in the range where the effect of emulsion inhomogeneity is minimized even at depth. The effect of this high primary-to-scatter ratio is manifest in measured sensitometric curves, which are invariant (to within 1.5%) with depth (to 20 cm in a phantom) and with field size (within the range of field diameters used in radiosurgery).

Radiochromic films have one or more thin microcrystalline layers of monomer which polymerize in response to irradiation. Currently available radiochromic films turn blue following exposure to radiation and require no chemical processing. The constituents of the film are essentially tissue equivalent.

There is a need for methods and systems for relatively quickly and accurately measuring the dose distributions provided by radiosurgery systems and, more generally, three-dimensional distributions provided by other systems.

SUMMARY OF INVENTION

This invention provides a method for creating a volumetric data set containing data representing a three-dimensional distribution of a physical quantity. The quantity may be, for example, the integrated dose produced within a volume by one or more radiation sources. The radiation sources may be sources in a radiosurgery system. The method comprises providing a plurality of spaced apart two dimensional analog sensors in fixed orientations; simultaneously creating a plurality of two dimensional analog images by exposing the plurality of sensors to the distribution; scanning the two dimensional analog images to yield digitized images; and, before scanning the analog images providing fiducial marks on each of the plurality of sensors, the fiducial marks identifying an order and sequence of the sensors. The sensors may be film. In specific embodiments of the invention the sensors are parallel, spaced apart sheets of X-ray film.

Preferably the sensors are generally planar so that each sensor measures a cross-section of the distribution. Each sensor is preferably parallel to and spaced apart from adjoining sensors. The fiducial marks are useful for automatically identifying the orientation and sequence of films within a set of films. The fiducial marks may be provided by exposing selected locations on the films, or other sensors to radiation, which may be light.

the digitized images are delivered to a programmed computer. The programmed computer locates the fiducial marks, and, from the fiducial marks, identifies a sequence of the digitized images. The method preferably includes determining from the fiducial mark whether an image of a sensor is correctly oriented and, if the image is not correctly oriented, applying one or more rotation or flip transformations until the image is correctly oriented. This causes the method to be insensitive to human error which might result in one or more images being placed out of sequence or in the wrong orientation. The fiducial mark on each of the sensors is preferably located along one edge of the sensor and, when the sensors are in the fixed orientations, all of the fiducial marks are located between a midpoint of one edge of the sensor and a corresponding corner of the sensor. Where the distribution is a dose distribution produced by a radiosurgery system, the method may include exporting a volumetric data set in a format which comprises landmarks which specify points in the volumetric data set corresponding to known locations in a coordinate system of the radiosurgery system. This facilitates coregistering the volumetric data set with an intended dose distribution.

Another aspect of the invention provides a computer system for creating a volumetric data set from a plurality of two-dimensional digitized images. The computer system comprises a processor and stored instructions which, when run on the processor, cause the processor to: for each of a plurality of two-dimensional digitized images locate a fiducial mark on the image; determine from a location of the fiducial mark whether the image is correctly oriented; if the image is not correctly oriented, apply one or more inversions and rotations to the image until it is correctly oriented; determine from a location of the fiducial mark the sequence of the image relative to the other images; and, populate a three dimensional array with data from the digitized images. Preferably the software further causes the processor to compute predicted values between points in the three dimensional array by interpolation.

Further features and advantages of the invention are described below.

BRIEF DESCRIPTION OF DRAWINGS

In figures which illustrate non-limiting embodiments of the invention:

FIGS. 7A, 7B, 7C and 7D show four scanned images of the same film in which FIG. 7A shows the film in the correct orientation and FIGS. 7B through 7D show the film in various incorrect orientations, the fiducial mark which indicates the correct orientation and sequence of the film can be seen;

DESCRIPTION OVERVIEW

This invention involves obtaining a number of two-dimensional analog images of a three-dimensional distribution of a physical quantity, digitizing those images and creating a three-dimensional (volumetric) data set from the digitized image data. The analog images are obtained using suitable two-dimensional sensors which respond to the physical quantity. For example, where the quantity is a dose of ionizing radiation the two-dimensional sensors may be sheets of X-ray film. It can be appreciated that creating a volumetric data set requires knowledge of the order and orientation of the two-dimensional images. The invention may be used in various applications in which the three-dimensional structure of a distribution of a physical quantity must be determined.

EXAMPLE

Measuring Dose Distributions in Radiosurgery

The following is an example of the invention being applied to measuring the dose distribution produced by a radiosurgery system in a measurement volume within an anthropomorphic phantom. The inventors have ascertained that for dosimetry of radiosurgical systems radiographic or radiochromic films may be arranged in stacks, separated by tissue equivalent spacers, to provide a series of two-dimensional images showing the dose distribution on a number of parallel planes in a dose distribution. The film may be, for example, X-Omat V film available from the Eastman Kodak Company. Suitable spacers may be made, for example, from polystyrene, SOLID WATER™ available from Gammex, Inc. of Wisconsin U.S.A., PLASTIC WATER™ available from Computerized Reference Imaging Systems, Inc. of Virginia U.S.A. or LUCITE™ available from E.I. DuPont de Nemours & Co. of Delaware, U.S.A.

The films are preferably rectangular and may be arranged within a cassette inside a tissue-equivalent phantom. The spacers may be, for example, approximately ⅛ inches (about 3.175 mm) in thickness. The cassette is held in a known desired position relative to the phantom. The phantom is held in a known desired position within a radiosurgical coordinate system of the radiosurgery system. Standard head rings or other immobilization devices may be used to hold the plantom in place within the radiosurgical coordinate system. A description of such a phantom and its use in volumetric dosimetry of radiosurgical fields are contained in U.S. patent application Ser. No. 09/436,917 filed 9 Nov. 1999 and entitled ANTHROPOMORPHIC FILM PHANTOM FOR THREE-DIMENSIONAL STEREOTACTIC RADIOSURGICAL DOSIMETRY, which is incorporated herein by reference. The cassette or other holder should hold each film in a known position relative to the dose distribution being measured. Preferably each film has two straight perpendicular edges which are both positively located in the cassette or other holder. These edges may be called "reference" edges.

After the films are created they must be digitized. Before the films can be digitized they must be removed from their cassette and processed (if they are radiographic films). These procedures present numerous opportunities for the order and orientations of the films to become mixed up. Keeping track of the order and orientation of films is particularly onerous where a large number of two-dimensional films are required to image the three dimensional distribution being studied with satisfactory resolution. There is a need for methods and systems for handling such films which are not susceptible to errors caused by accidental changes in order and orientation.

Figure 1:
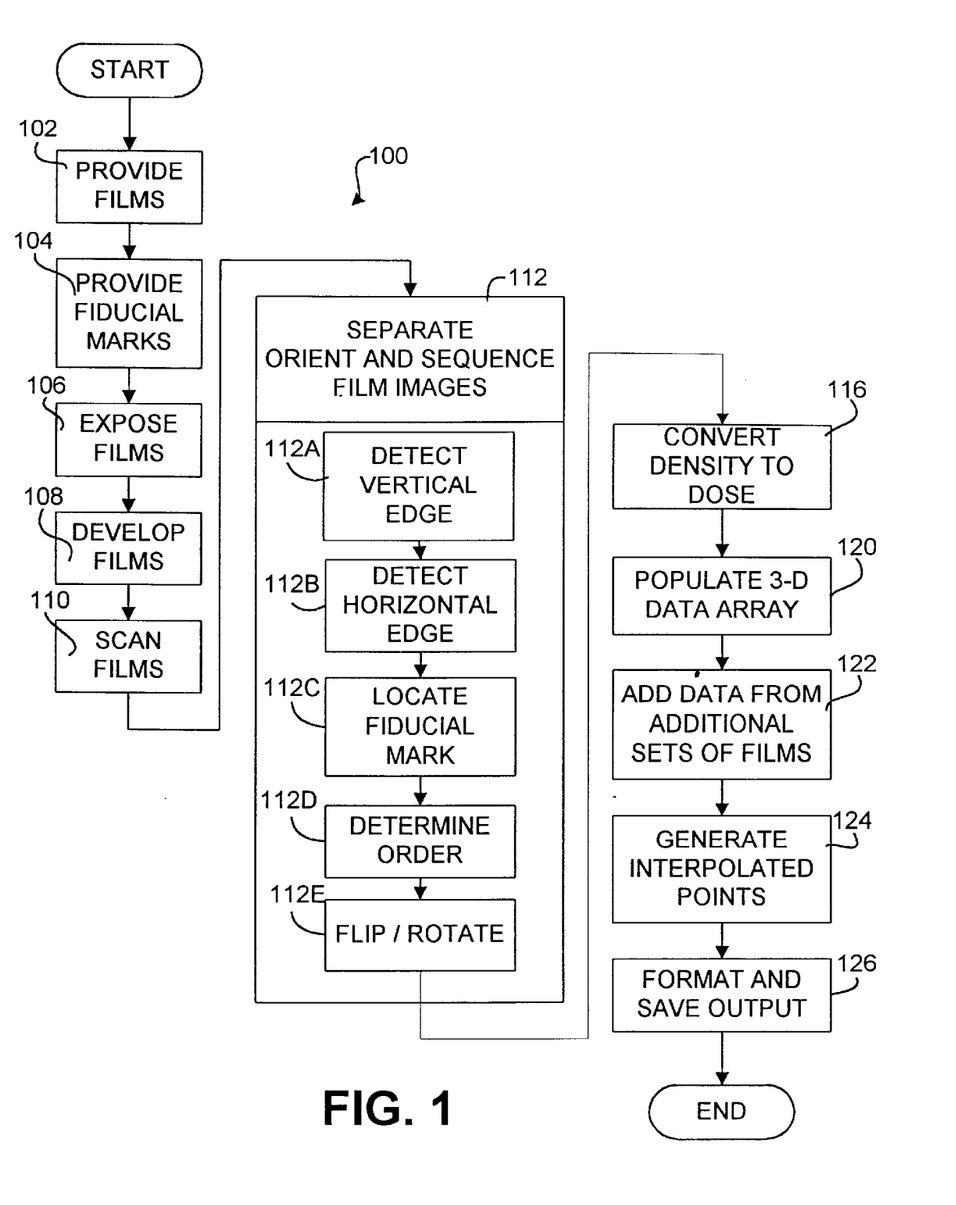
FIG. 1 is a flowchart illustrating the various steps of the automated process of this invention.
Figure 2:
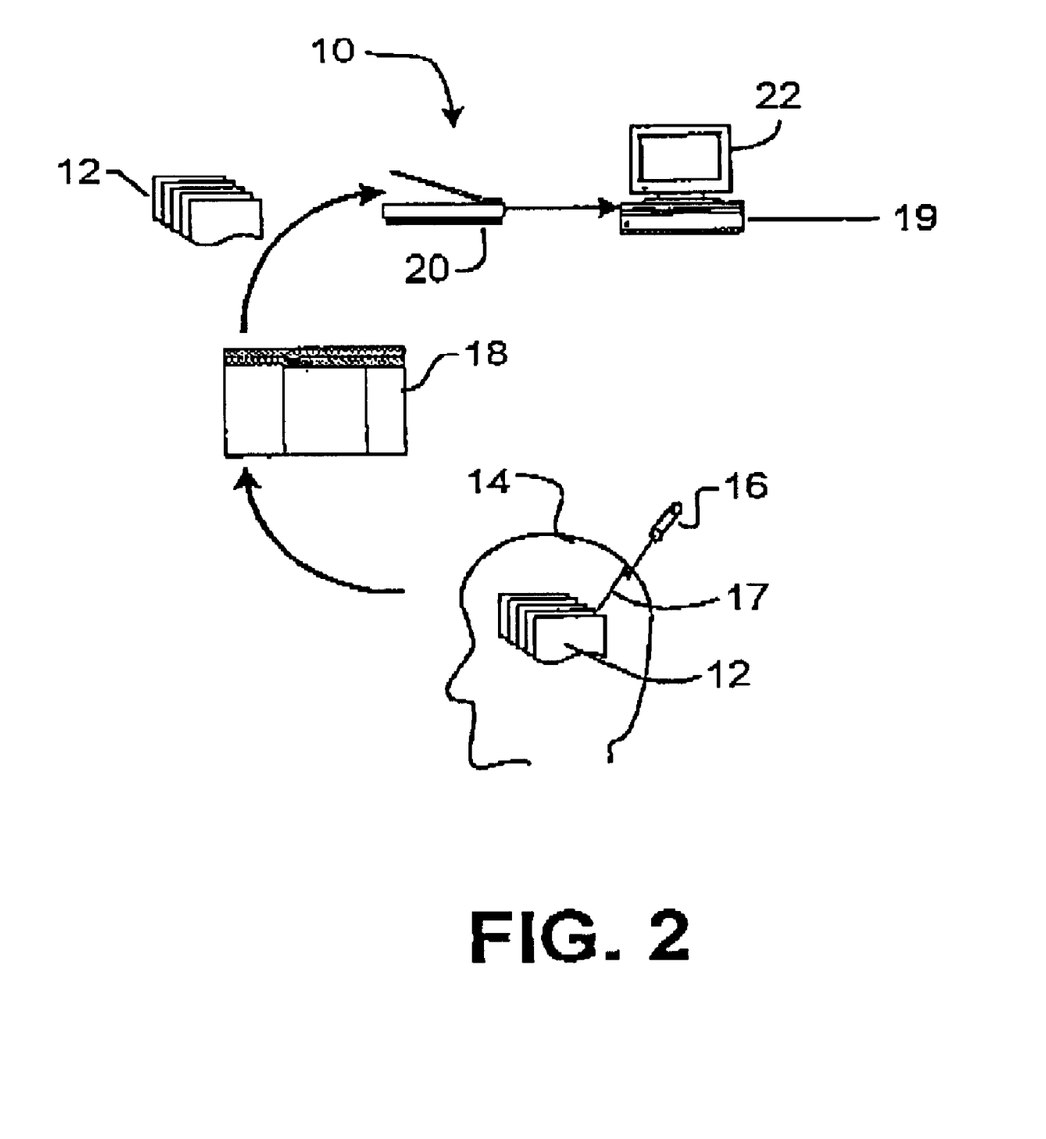
FIG. 2 is a schematic diagram illustrating a sequence of steps for acquiring two-dimensional images for use in this invention.

FIG. 1 illustrates a method 100 according to the invention. Method 100 includes providing (step 102) a plurality of radiation-sensitive films 12 (FIG. 2). Each film 12 is marked with a fiducial mark 18 (step 104). The fiducial mark indicates the sequence of the film relative to the other films 12 and its orientation. The fiducial marks 18 are detectable by a digitizer, as described below.

Figure 3:
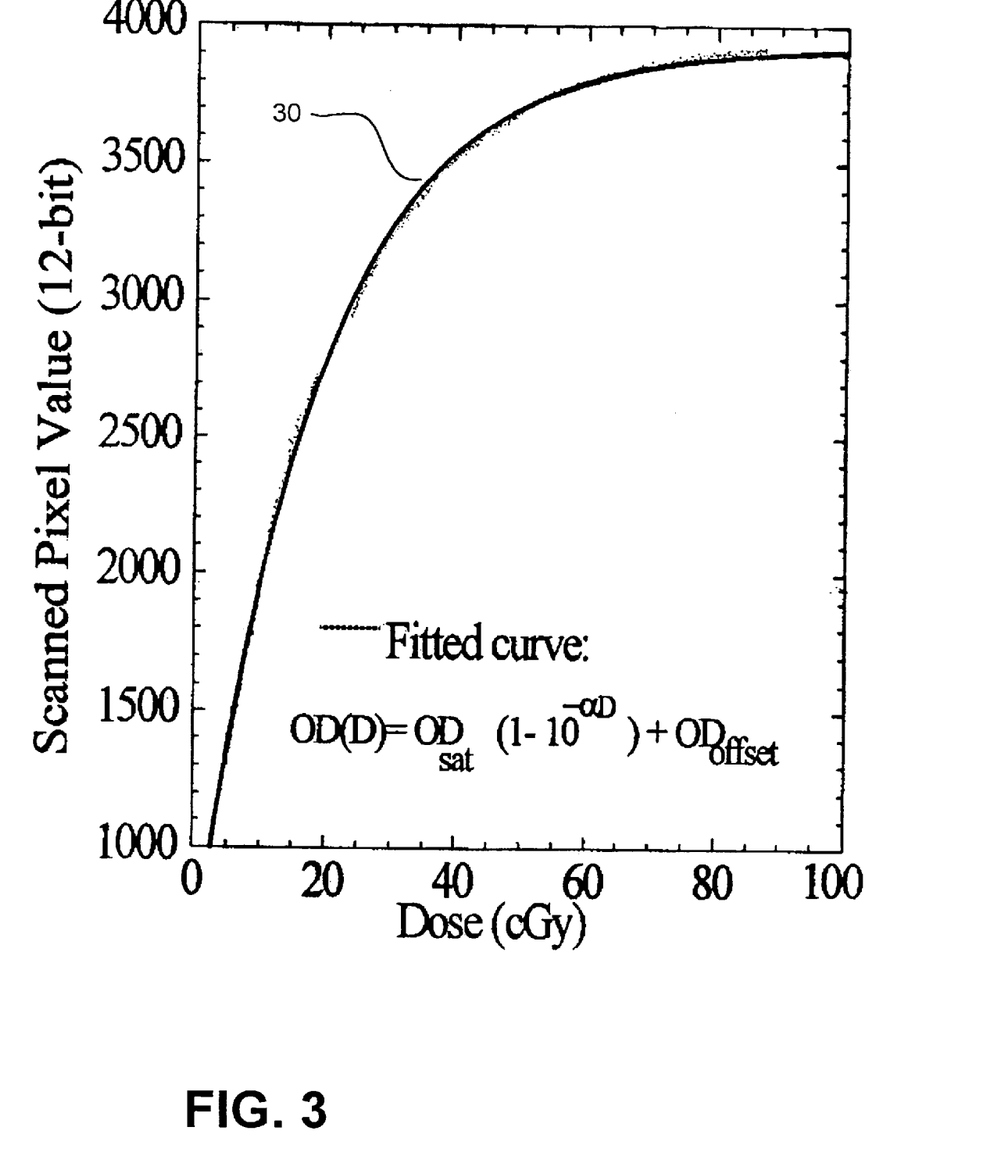
FIG. 3 is a curve illustrating the relationship between dose and optical density for an exposed radiographic film.

Films 12 are exposed to a radiation field 17 produced by a radiosurgical system 16 in step 106. The films are held in a known position relative to the radiosurgery coordinate system during exposure so that the measured dose distribution can be coregistered with an intended dose distribution. If necessary, the films may be processed (step 108) in a suitable processor 19 to provide a series of two-dimensional images representing the integrated dose provided in different planes through the dose distribution being studied. Processor 19 is typically an automatic film processor. Whether or not film processing is necessary depends upon the type of film being used. The optical density of the resulting images has a spatial distribution which is related to the dose delivered by a calibration function which depends upon the film being used and, possibly, on the characteristics of the radiation being studied. FIG. 3 is an example of a calibration curve 30 typical of a radiographic film. The equation in FIG. 3 describes this curve where OD is the scanned pixel value, D is the absorbed dose, and $OD_{sat}$ and $OD_{offset}$ are fitting parameters. This equation is inverted for direct conversion of pixel value to dose.

Figure 6:
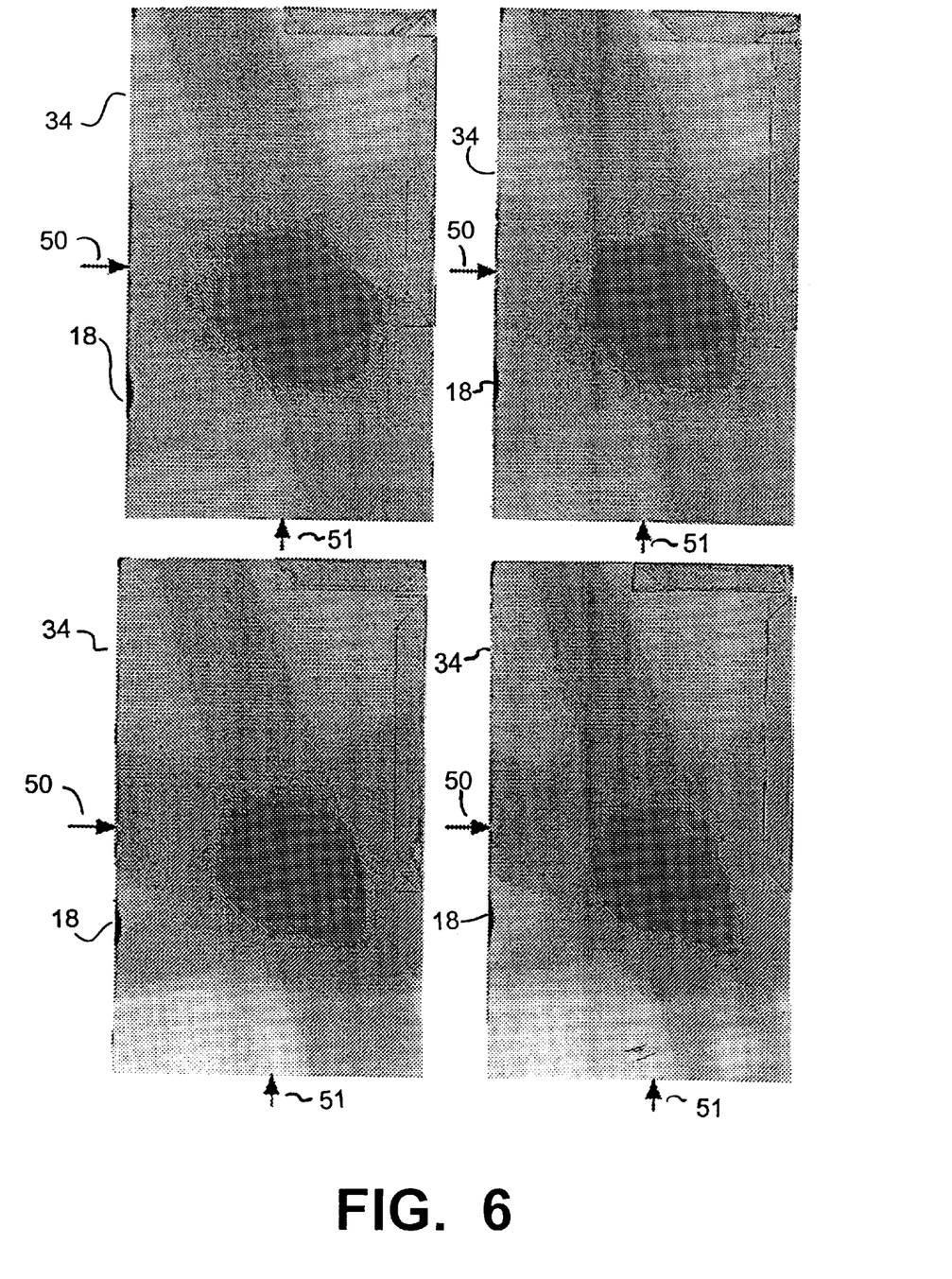
FIG. 6 is an example of a multiple film scanned image derived from digitally scanning a batch of four films.

After films 12 have been imaged they are digitized (step 110) at a suitable spatial resolution. It is a feature of preferred embodiments of this invention that the films do not need to be digitized in any specific order or orientation. Digitization of films may be achieved, for example, by using laser scanning densitometers, infrared scanning densitometers, charge-coupled device (CCD) based scanners or CCD camera systems. Suitable film digitization systems are commercially available and are known to those skilled in the art. A number of films may be digitized simultaneously, for example, by arranging the films on the bed of a suitably large flat-bed scanner 20. FIG. 6 shows a single scanned image which includes images of four films 12 from one set of films. Scanning multiple films 12 simultaneously expedites the digitizing step. The digitized image or images, which include both portions from which information may be extracted about the distribution under study and portions which include digitized images of the fiducial marks 18, are provided to a computer 22.

Software in computer 22 analyses the digitized images. The software first separates, orients and sequences the scanned images (step 112). This may be done, for example, by detecting vertical and horizontal edges (steps 112A and 112B) of exposed films in the scanned images. If one or more of the scanned images contains images of more than one film 12 then it is necessary to extract individual images from the multiple film image. This extraction may be done using an edge-detection algorithm which searches the multiple film image to locate the boundaries of each individual film image. The images of individual films 12 can then be separately processed. The image of each film 12 may be stored in a separate block of memory or in a separate file so that the individual images can be conveniently manipulated. Detecting edges of the images and separating multiple images may be accomplished using straight forward well known image processing techniques since the exposed films have a density greater than that of surrounding background areas.

The software includes an image extraction algorithm which searches in the regions denoted by the black arrows 50, and 51 (FIG. 6) for a pixel, or region of pixels exceeding a set pixel threshold. The software then locates the fiducial mark 18 in each scanned image. This is facilitated because the locations of the fiducial mark is known. For example, the fiducial marks may be located at different distances along a specified edge of each film 12. The location of the fiducial mark identifies the reference edges (i.e. identifies the proper orientation of the image).

The image extraction algorithm locates the coordinates of the bottom left corners of the portion of the image which relates to each individual film. These corners lie at the intersection of two reference edges. The positions of the edges provides the software with the information necessary to extract each individual film image for storage in a separate memory location and subsequent processing. These corners can conveniently be used as origins with respect to which the positions of scanned pixels in each film can be reported. The locations of these origins may be located precisely by fitting lines to the reference edges of the film's image and noting the intersection of the lines.

As soon as the software has detected the position of fiducial marks 18 the sequence and orientation of the scanned images can be determined (step 112D). In the illustrated embodiment the orientation of the scanned images is identified by the edge along which the fiducial mark is located and by which half of the edge the fiducial mark is located in. The sequence of the fiducial mark is indicated by the position of the fiducial mark along the edge.

Figure 7A:
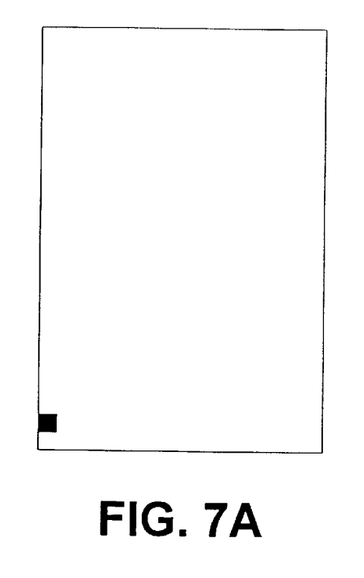
Figure 7B:
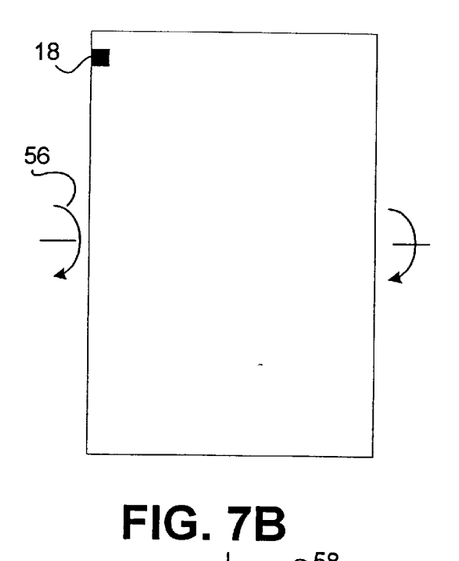
Figure 7C:
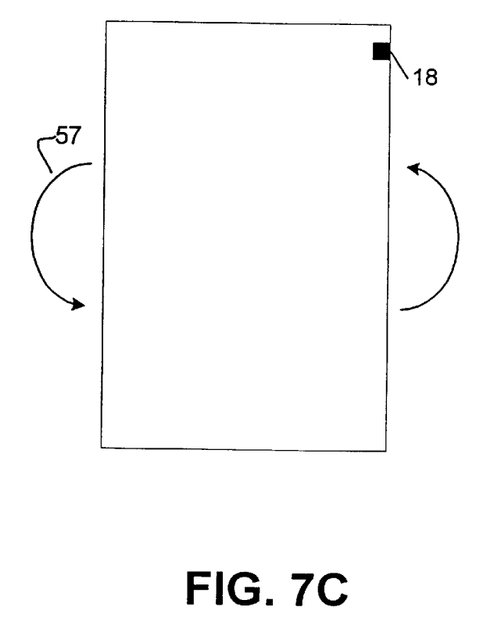
Figure 7D:
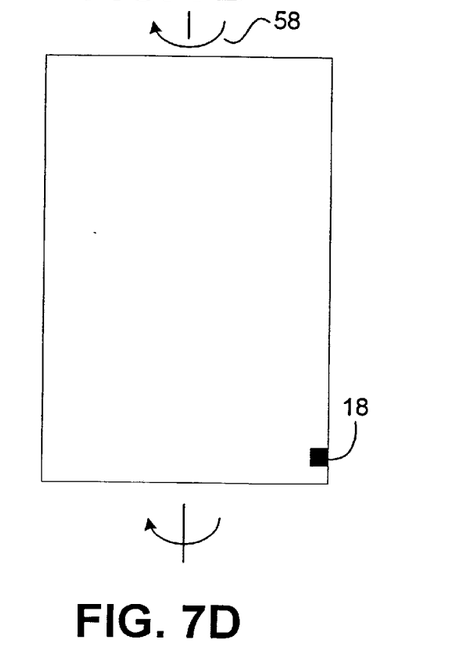

If necessary the software rotates and/or flips each image so that it is properly oriented (step 112E). For example, if a properly oriented image of a film is oriented as shown in FIG. 7A then an image of the same film oriented as shown in FIG. 7B should be flipped vertically (as viewed in FIG. 7B as indicated by arrow 56. An image of the same film oriented as shown in FIG. 7C should be rotated by 180 degrees as indicated by arrow 57. An image of the same film oriented as shown in FIG. 7D should be flipped horizontally as indicated by arrow 58. Equivalent transformations could also be used to properly orient the images of FIGS. 7B to 7D.

The measured density of each pixel (or selected pixels or regions) of the digitized image can then be converted to an integrated radiation dose (energy absorbed per unit mass) with the use of a calibration function appropriate to the particular film 12 being used (step 116). Other transformations, as desired, may be applied to each image in the set.

The dose data resulting from step 116 can then be entered into the cells of a three-dimensional data structure (step 120). Preferably, each cell of the data structure contains a number representing the integrated dose measured in a small volume surrounding a point in space. The points to which the cells correspond are preferably located on a three-dimensional rectilinear grid. Not all cells of the data structure will necessarily correspond to points which are imaged on one of films 12. Many parts of the three dimensional distribution are in between adjacent films 12. Optionally data from additional sets of films 12 may be acquired as described above and used to fill out the data structure (step 122). During exposure the planes of the additional sets of films are either translated or rotated from the positions of the films in the original set of films so that they have a different orientation from the planes of the original sets of films. The additional sets of film image some points not imaged by the first set of films 12.

The dose values in any remaining cells of the array can then be populated by interpolation (step 124) based upon the values in adjoining cells. That is, the array may be 're-sampled'. Preferably a bicubic interpolation algorithm is used to calculate interpolated values. Bicubic interpolation provides an estimate of a value of a quantity at an arbitrary spatial location from known values of the quantity, and spatial derivatives of the quantity values, at four neighbouring locations. The bicubic interpolation is preferably repeated in x-y, x-z and y-z planes to estimate the measured quantity using the neighbouring measured information in three dimensions. Descriptions and examples of bicubic interpolation algorithms may be found, for example, in W. Press et al. *Numerical Recipies in C*, Cambridge University Press, 1992. The spatial frequency of the interpolated images may be set arbitrarily and may be significantly greater than the spatial frequency of images in a single image set.

The three-dimensional dose distribution data in the array can then be displayed on a suitable monitor and stored in a convenient file format. In medical imaging the DICOM (Digital Imaging and Communications in Medicine) format is very commonly used. In addition to the image data itself, this format encodes the spatial position, resolution and size of each individual image. Preferably the system permits a user to cause the software to export a record of the entire spatial dose distribution as a series of DICOM images, whereby each DICOM image represents a slice of user-defined thickness through the measured dose volume and the separation between slices is also defined by the user. This final collection of image information thus contains a complete description of the measured quantity throughout the measurement volume.

The resulting dose distribution data may be spatially coregistered in treatment planning software for comparison with an intended dose distribution. Coregistration may be achieved, for example, by employing existing CT/MRI image fusion tools. Such software tools are commonly featured in radiosurgery treatment planning software packages. For example, a CT image set of a phantom 14 (containing cassette 40) is obtained and loaded into memory by the treatment planning software. The CT scanner used to acquire the image is aligned with the radiosurgical coordinate system so that the positions of items imaged by the CT scanner are known. In this CT image set, the inner surfaces of cassette 40 which define the positions of the reference edges of each film 12 are visualised. Prior to exporting the DICOM image set containing the measured dose volume to the treatment planning software, landmarks which correspond to known points in the radiosurgical coordinate system are preferably included in the DICOM images. These marks may consist of, for example, lines or L-shaped marks at the corners of known planes in the coordinate system. Once loaded into the memory, the image set containing the measured dose distribution may be translated, rotated and scaled as necessary to spatially align the landmarks, which may for example indicate reference edges of the films used to measure the dose distribution, with the known positions for those landmarks in the radiosurgical coordinate system. For example, the image set may be positioned and scaled so that landmarks corresponding to the reference edges of films 12 align with the previously measured positions of the inner surfaces of cassette 40 against which the reference edges are registered, as required. When coregistered the actual and intended dose distributions share the same spatial scale, spatial location and spatial orientation. This permits direct comparison between the measured and intended dose distributions.

Any deviations of the actual distribution from the intended dose distribution can thereby by identified before a radiosurgery treatment is delivered to a patient. The radiosurgery plan can be adjusted to correct these deviations.

Fiducial Marks

Fiducial marks 18 (which may be called "indexing landmarks") are preferably located along a specified edge of each film 12. The position of a fiducial mark 18 along the edge indicates the sequence of each film 12. If the range of positions of fiducial marks 18 is limited to one half of the side then the correct orientation of each film 12 can be obtained by rotating and/or flipping the image so that the detected fiducial mark is located in the proper half of the edge.

Figure 4:
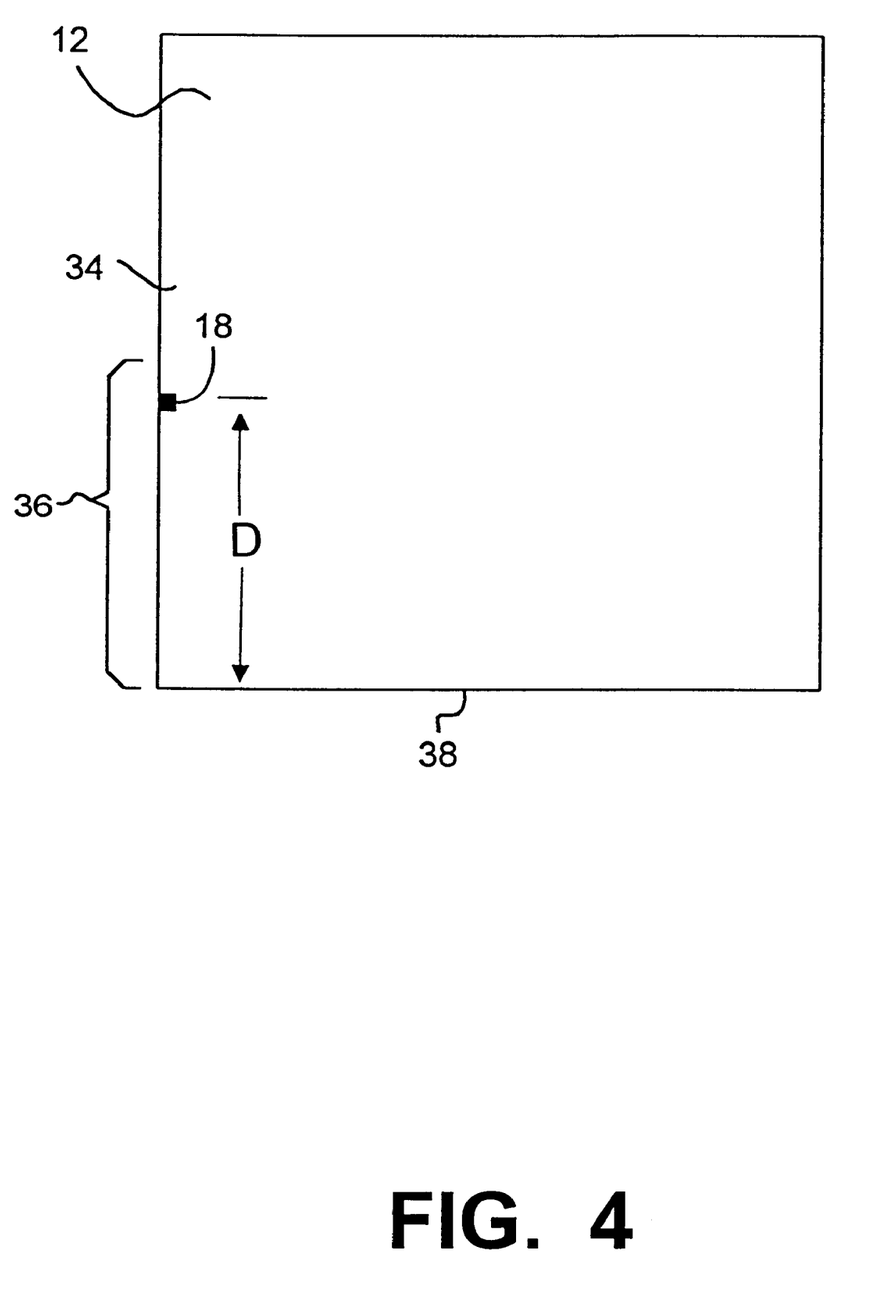
FIG. 4 is a film marked with a fiducial mark for use in the invention.

FIG. 4 shows a film 12 having an edge 34 along which is located a fiducial mark 18. Fiducial mark 18 is an area of increased optical density. Each film 12 has a fiducial mark 18 located at a different position in the range 36 which occupies one half of side 34. FIG. 6 shows four film images from a single image set. In this example the distance of the fiducial marks from the bottom edge of each film indicates the order of that film within the film set. Software in computer 22 can readily detect fiducial marks 18 and thus can automatically order films 12 in sequence.

Figure 5:
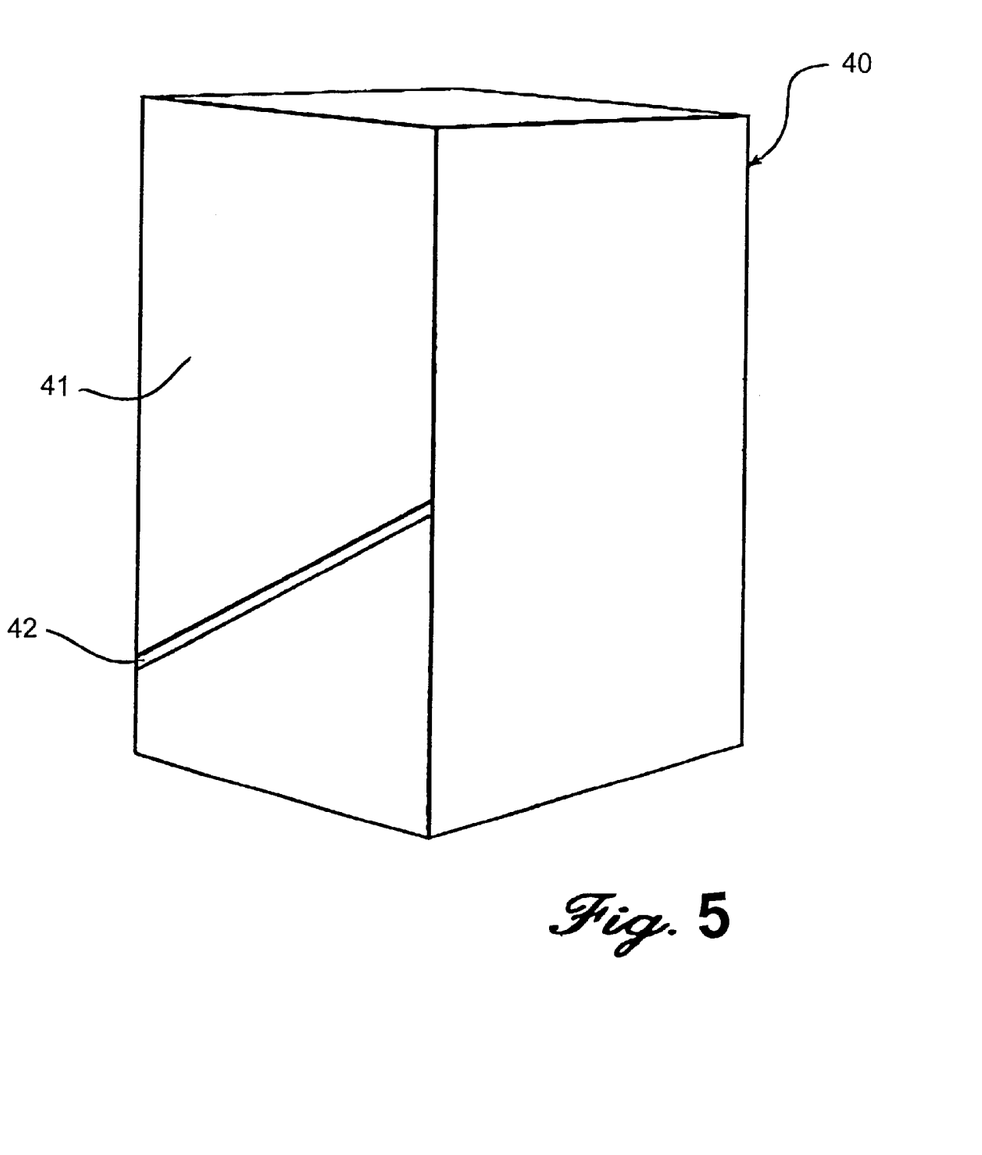
FIG. 5 is an isometric view of a film cassette which may be used to provide fiducial marks on X-ray films for use in the invention.

Fiducial marks 18 may be created in various ways. In a preferred embodiment of the invention films 12 are held within an opaque cassette while they are exposed to radiation. FIG. 5 shows a possible cassette 40. Films 12 are held inside cassette 40 so that their edges 34 are against the inside of a face 41. An optically translucent stripe 42 is provided in a lower half of face 41. Stripe 42 is diagonal so that it intersects the edge 34 of each film 12 a different distance away from the corner between edges 34 and 38. Since radiographic film is somewhat sensitive to visible light, the portions of films 12 which are immediately adjacent to stripe 42 will be exposed to create optically dense regions which can serve as fiducial marks.

Where films 12 are not light sensitive then fiducial marks may be created in other ways. For example, for radiochromic films which are not very light sensitive, a series of fiducial marks may be created by irradiating a stack of films with an angled collimated beam of high energy radiation. The radiation beam creates exposed spots on each film which may be used as fiducial marks. The fiducial marks should be outside the measurement volume. Fiducial marks may also be created by mechanically notching edges of films 12, punching small holes in films 12, or marking films 12 with ink, small adhesive stickers, or the like.

In a variation of the invention the fiducial marks each comprise a different symbol, such as a number, and the software determines the order of the scanned images by performing optical character recognition on the symbols. Orientation may be ascertained from the observed locations and/or orientations of the symbols.

The fiducial marks may be applied before, during or after the exposure of films 12. The fiducial marks should be applied before films 12 are removed from their cassette 40 so that the set of films 12 cannot become mixed up in order or orientation before the fiducial marks 18 are applied.

Use of Multiple Film Sets

A single set of films typically comprises a set of 10 to 20 films but may include more or fewer films. In some cases a single set of films will not provide sufficient spatial resolution. Preferred embodiments of the invention permit multiple sets of films to be exposed and digitized. The resulting data can then be fused to produce composite volumetric distribution data.

Figure 8A:
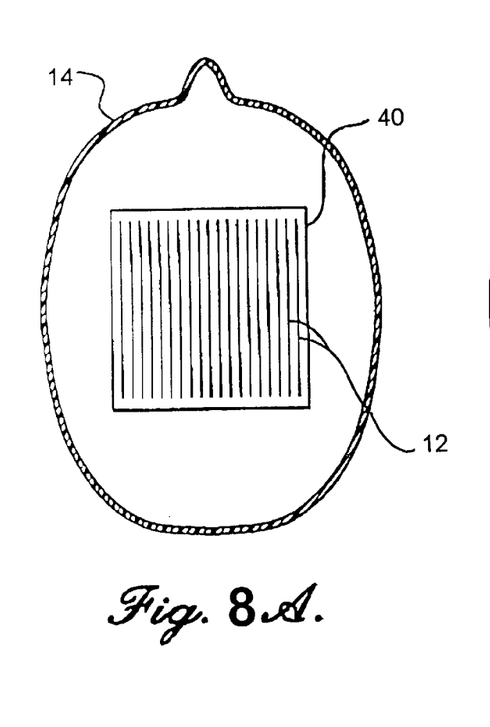
FIGS. 8A, 8B and 8C are top transverse sectional views through a phantom and film cassette holding sets of parallel, spaced apart films with the cassette in three different orientations.
Figure 8B:
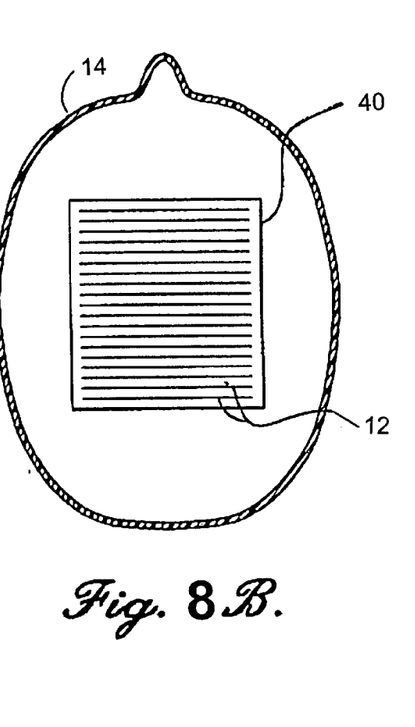
Figure 8C:
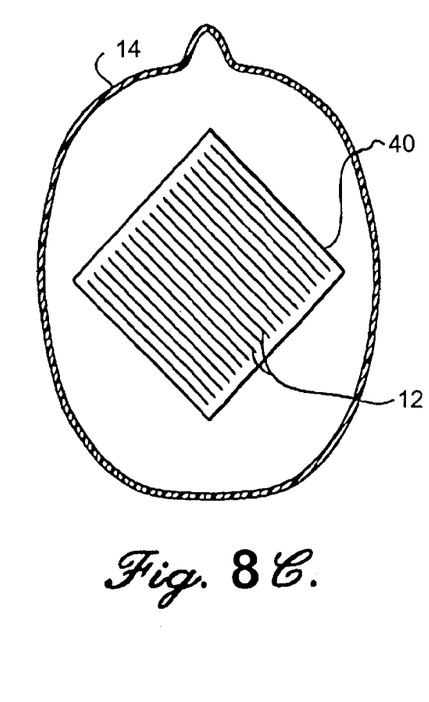

For example, FIGS. 8A, 8B and 8C each show a phantom 14 having a film cassette 40 mounted at a known location inside it. The cassette is oriented differently in each of FIGS. 8A, 8B and 8C. Each set of films is separately digitized. The data from the different sets of films can be combined at step 122. Where there is redundancy between two or more image sets (i.e. the dose received by a particular voxel is measured by two or more image sets) the system may compute a mean value of the dose for the voxel in question and store the mean value in the appropriate location in the array.

Software

There are many equivalent forms of computer software which may be used in the practice of this invention. In general, what is required is computer software which, when run on a suitable computer 22, causes a processor of the computer (the processor may include multiple processing units such as microprocessors) to create a volumetric data set from a plurality of two-dimensional digitized images. The computer software may be stored in any way which makes it accessible to the processor. When the software is run on the processor it causes the processor to:

a) for each of a plurality of two-dimensional digitized images locate a fiducial mark on the image;

b) determine from a location of the fiducial mark whether the image is correctly oriented;

c) if the image is not correctly oriented, apply one or more inversions and rotations to the image until it is correctly oriented;

d) determine from a location of the fiducial mark the sequence of the image relative to the other images; and, e) populate a three dimensional array with data from the digitized images.

Figure 9A:
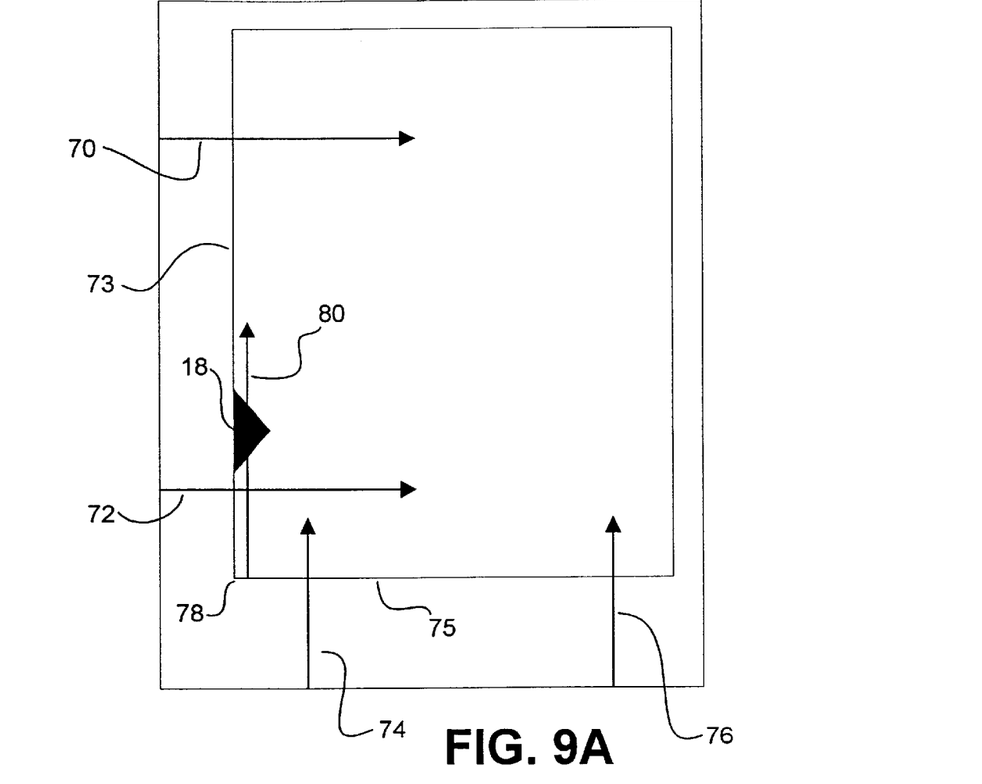
FIG. 9A is a diagram illustrating lines along which digitized optical density values may be checked to locate edges of an image of a sensor and a fiducial mark; and, FIGS. 9B and 9C are plots of optical density as a function of position along some of the lines of FIG. 9A.
Figure 9B:
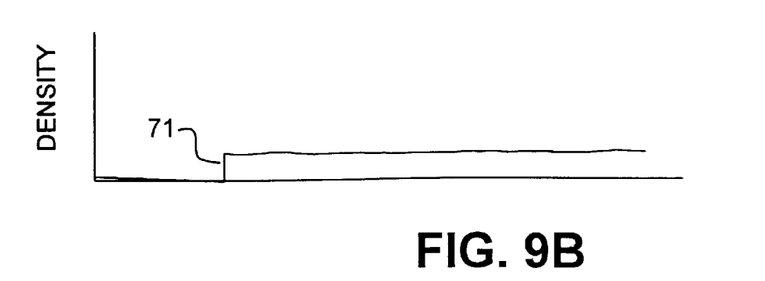

In a currently preferred embodiment, the software locates the fiducial mark in an image by locating an edge of a film or other sensor in the image. This may be done by checking density values along two, and preferably more lines crossing the image. For example the software may cause the processor to check the density values along lines 70 and 72 of FIG. 9A. The density along each of these lines will show a step 71 (FIG. 9B) corresponding to the image of the edge 73 of film 12. Where the edge is located at more than two points a line can be fit to the points to locate edge 73 to sub-pixel accuracy.

Figure 9C:
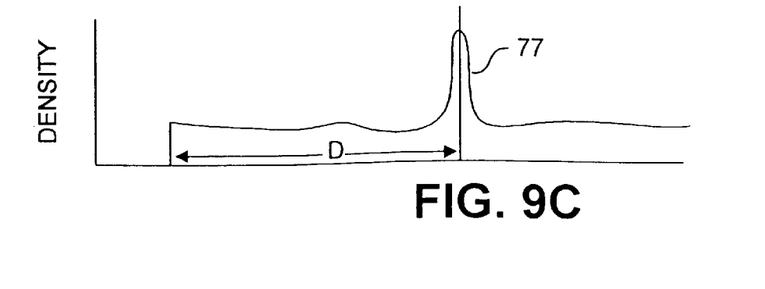

The image 75 of a second edge of film 12 may be lo ted in a similar fashion. The intersection of linear edges 73 and 75 defines an origin point 78. The image of fiducial mark 18 may be locate by checking density values along a line 80 lying parallel to edge 73. FIG. 9C shows the variation of density values along line 80. The position of peak 77 corresponds to the distance D from origin point 78 to the fiducial mark 18. If no peak 77 is located then the image must not be properly oriented. The software can cause the processor to rotate the image and then to try again to locate the fiducial mark.

The software can determine the order of multiple images in a set of images by comparing the positions of their fiducial marks as measured from their respective origin points 78. The spacing between films 12 may be supplied by a user or pre-set in the software.

After origin points 78 have been located then the software can cause the processor to look up density values in each image at locations measured relative to the locations of origin points 78 and to place these values in a three dimensional array at locations corresponding to spatial positions within the original three-dimensional dose distribution being investigated.

The software preferably further causes the processor to compute predicted values for the density at locations within the array which do not correspond to a spatial position on any of films 12 by interpolation. The software preferably includes an algorithm for performing a bi-cubic interpolation and causes the processor to perform the bi-cubic interpolation algorithm to compute the predicted values.

Where the computer system is being used in conjunction with a radiosurgery dose planning system the software preferably provides the function of coregistering a measured volumetric dose distribution with a desired dose distribution so that differences between the desired and measured dose distributions can be observed.

As will be apparent to those skilled in the art in the light of the foregoing disclosure, many alterations and modifications are possible in the practice of this invention without departing from the spirit or scope thereof. For example, an application of this invention to measuring the dose distribution delivered by a radiosurgical system has been described by way of example. The invention has application in other areas where it is necessary to determine a three-dimensional distribution by taking and combining multiple two-dimensional measurements. Accordingly, the scope of the invention is to be construed in accordance with the substance defined by the following claims.

What is claimed is:

1. A method for creating a volumetric data set containing data representing a three-dimensional distribution of a physical quantity, the method comprising:

a) providing a plurality of spaced apart two dimensional analog sensors (12) in fixed orientations;

b) simultaneously creating a plurality of two dimensional analog images by exposing the plurality of sensors to the distribution;

c) scanning the two dimensional analog images to yield digitized images;

d) before scanning the analog images providing fiducial marks (18) on each of the plurality of sensors, the fiducial marks identifying an order and sequence of the sensors.

2. The method of claim 1 wherein the sensors are generally planar and each sensor is parallel to and spaced apart from adjoining sensors.

3. The method of claim 1 wherein the sensors comprise sheets of radiation sensitive film.

4. The method of any one of claims 1 wherein the fiducial marks are provided by exposing the sensors to radiation.

5. The method of any one of claims 1 comprising providing the digitized images to a programmed computer, in the programmed computer locating the fiducial marks, and, from the fiducial marks, identifying a sequence of the digitized images.

6. The method of claim 5 comprising determining from the fiducial mark whether an image of a sensor is correctly oriented and, if the image is not correctly oriented, applying one or more rotation or flip transformations until the image is correctly oriented.

7. The method of claim 5 comprising scanning a plurality of sensors into a single digitized image and, in the programmed computer, separating the images of the plurality of sensors into individually manipulable images.

8. The method of claim 3 wherein the sensors are rectangular.

9. The method of claim 8 wherein the fiducial mark on each of the sensors is located along one edge of the sensor and, when the sensors are in the fixed orientations, all of the fiducial marks are located between a midpoint of the edge and a corresponding corner of the respective sensor.

10. The method of claim 2 comprising repeating: providing a plurality of spaced apart two dimensional analog sensors in fixed orientations; simultaneously creating a plurality of two dimensional analog images of the distribution by exposing the plurality of sensors to the distribution; and scanning the two dimensional analog images to yield digitized images; wherein, each of the sets of sensors is exposed to the distribution so that its sensors sample points in the distribution not sampled by sensors in other ones of the sets of sensors and fusing data from each of the sets together to provide the volumetric data set.

11. The method of claim 10 wherein the distribution is a dose distribution produced by a radiosurgery system and the method comprises exporting a volumetric data set in a format which comprises landmarks which specify points in the volumetric data set corresponding to known locations in a coordinate system of the radiosurgery system.

12. The method of claim 11 wherein the format is a DICOM format.

13. A computer system for creating a volumetric data set from a plurality of two-dimensional digitized images the computer system comprising a processor and stored instructions which, when run on the processor, cause the processor to:

a) for each of a plurality of two-dimensional digitized images locate a fiducial mark on the image;

b) determine from a location of the fiducial mark whether the image is correctly oriented;

c) if the image is not correctly oriented, apply one or more inversions and rotations to the image until it is correctly oriented;

d) determine from a location of the fiducial mark the sequence of the image relative to the other images; and, e) populate a three dimensional array with data from the digitized images.

14. The computer system of claim 13 wherein the software further causes the processor to compute predicted values between points in the three dimensional array by interpolation.

15. The computer system of claim 14 wherein the software includes an algorithm for performing a bi-cubic interpolation and the software causes the processor to perform the bi-cubic interpolation algorithm to compute the predicted values.

16. The computer system of claim 15 wherein the software causes the processor to locate the fiducial mark on the image by detecting an edge in the image and searching along the edge for the fiducial mark.

17. The computer system of claim 15 wherein the software causes the processor to locate first and second intersecting reference edges in the image and to determine an origin point where the reference edges intersect.

18. The computer system of claim 17 wherein the software causes the processor to populate the array with data from locations on the images measured relative to the origin points of the images.

19. The method of claim 2 wherein the sensors comprise sheets of radiation sensitive film.

20. The method of claim 5 wherein the sensors are rectangular.

* * * * *